(12) United States Patent
Perry et al.

(10) Patent No.: US 10,699,808 B2
(45) Date of Patent: Jun. 30, 2020

(54) COST OF HEALTHCARE ANALYTICS PLATFORM

(71) Applicant: Accenture Global Solutions Limited, Dublin (IE)

(72) Inventors: Thomas D. Perry, Vienna, VA (US); Meghan Hildebrand Fotopoulos, Philadelphia, PA (US); Kreshnik Ahmeti, Villa Park, IL (US); Liubao Wei, Chapel Hill, NC (US); Xavier Ferragut, Miami, FL (US); Santhosh George, Aurora, CO (US); Yinghong Fu, Dallas, TX (US)

(73) Assignee: Accenture Global Solutions Limited, Dublin (IE)

( * ) Notice: Subject to any disclaimer, the term of this patent is extended or adjusted under 35 U.S.C. 154(b) by 388 days.

(21) Appl. No.: 15/369,329

(22) Filed: Dec. 5, 2016

(65) Prior Publication Data

US 2018/0157797 A1 Jun. 7, 2018

(51) Int. Cl.
*G06F 7/60* (2006.01)
*G06F 17/10* (2006.01)
*G06F 17/50* (2006.01)
*G16H 40/20* (2018.01)

(52) U.S. Cl.
CPC ............ *G16H 40/20* (2018.01); *G06F 17/50* (2013.01)

(58) Field of Classification Search
None
See application file for complete search history.

(56) References Cited

U.S. PATENT DOCUMENTS 8,805,857 B2  8/2014  Bhammar et al.
2004/0122708 A1* 6/2004 Avinash ................ G06Q 10/10
                                                        705/2

(Continued)

FOREIGN PATENT DOCUMENTS

WO    WO 2016/138102    9/2016

OTHER PUBLICATIONS

Australian Office Action for Appln. No. 2017265075, dated Feb. 12, 2019, 8 pages.

(Continued)

*Primary Examiner* — Cedric Johnson
(74) *Attorney, Agent, or Firm* — Fish & Richardson P.C.

(57) ABSTRACT

Implementations directed to identifying variables affecting a cost of healthcare include actions of receiving data from a plurality of data sources, the data relating to cost of providing healthcare, providing a data model based on the data, processing the data model using non-parametric analysis to provide a non-parametric result, the non-parametric result including a first and second variable, automatically processing the data model to correlate at least the first variable of the non-parametric result to the second variable of the non-parametric result to provide a correlation result, processing the correlation result using parametric analysis to provide a parametric result including at least one variable that affects the cost more than one or more other variables of a plurality of variables of the data model, and providing at least one data visualization for display, the at least one data visualization providing at least one graphical representation of the parametric result.

17 Claims, 6 Drawing Sheets

(56) References Cited

U.S. PATENT DOCUMENTS

| | | | |
|---|---|---|---|
| 2005/0080462 A1* | 4/2005 | Jenkins | G06F 19/3475 607/58 |
| 2005/0182659 A1* | 8/2005 | Huttin | G06F 19/328 705/2 |
| 2008/0046292 A1 | 2/2008 | Myers et al. | |
| 2010/0267052 A1* | 10/2010 | Gelber | C12Q 1/6883 435/7.1 |
| 2013/0005596 A1* | 1/2013 | Gong | C12Q 1/6883 506/9 |
| 2013/0085769 A1 | 4/2013 | Jost et al. | |
| 2013/0144642 A1* | 6/2013 | Bessette | G06Q 50/22 705/2 |
| 2016/0092641 A1* | 3/2016 | Delaney | G16H 50/70 705/3 |
| 2016/0253687 A1* | 9/2016 | Wei | G06Q 30/0202 705/3 |

OTHER PUBLICATIONS

Data Cleansing, [online article]. [retrieved from the Internet on Mar. 8 2019]. <URL: https://web.archive.org/web/20160403054258/https://en.wikipedia.org/wiki/Data_cleansing#The_process_of_data_cleansing> published on Apr. 3, 2016 as per Wayback Machine, 5 pages.

Australian Office Action for Application 2017265075, dated Apr. 13, 2018, 9 pages.

Australian Office Action for Appln. No. 2017265075, dated Aug. 23, 2018, 6 pages.

Australian Office Action for Appln. No. 2017265075, dated Mar. 29, 2019, 4 pages.

* cited by examiner

COST OF HEALTHCARE ANALYTICS PLATFORM

BACKGROUND

Data analytics can be used to provide insights into factors influencing outcomes. In an example context, healthcare, it can be difficult to determine factors influencing, for example, cost of healthcare. For example, insurance companies paying healthcare claims may need to understand factors influencing changes (e.g., increases) in a time- and technology-efficient manner. In this example context, data analysis is performed in disparate systems using at least partially manual processes. This results in inefficiencies in both time and any underlying technology used to perform the analyses. For example, a technical challenge includes processing data that is in disparate data formats (e.g., data provided from the disparate data sources is in disparate formats).

SUMMARY

Implementations of the present disclosure are generally directed to identifying one or more variables affecting a cost of healthcare. More particularly, implementations of the present disclosure are directed to providing time- and technology-efficient data analysis identifying one or more variables affecting a cost of healthcare.

In some implementations, actions include receiving data from a plurality of data sources, the data relating to cost of providing healthcare, providing a data model based on the data, automatically processing the data model using non-parametric analysis to provide a non-parametric analysis result, the non-parametric analysis result including a first variable, and a second variable, automatically processing the data model to correlate at least the first variable of the non-parametric analysis result to the second variable of the non-parametric analysis result to provide a correlation result, automatically processing the correlation result using parametric analysis to provide a parametric analysis result, the parametric result including at least one variable that affects the cost of healthcare more than one or more other variables of a plurality of variables of the data model, and providing at least one data visualization for display, the at least one data visualization providing at least one graphical representation of the parametric analysis result. Other implementations of this aspect include corresponding systems, apparatus, and computer programs, configured to perform the actions of the methods, encoded on computer storage devices.

These and other implementations can each optionally include one or more of the following features: actions further include providing an initial data model based on the data received from the plurality of data sources, and selectively deleting one or more data records from the initial data model to provide the data model; the non-parametric analysis result includes a sub-set of variables of the plurality of variables, each variable in the non-parametric analysis result having a respective score that exceeds a threshold score; the respective score includes a p-value; the correlation result includes a plurality of sets of variables, each set of variables in the correlation result having a respective score indicating a strength of correlation between variables in the set of variables that exceeds a threshold score; the data model includes a plurality of tables that are populated with a plurality of data values for each variable of the plurality of variables; and actions further include storing each of the non-parametric analysis result, the correlation result, and the parametric analysis result in a database, and providing one or more data visualizations for each of the non-parametric analysis result, and the correlation result.

Implementations of the present disclosure provide one or more of the following example advantages. In some examples, implementations of the present disclosure accommodate various data by applying analytical processes that identify significant costs in the healthcare context more rapidly and accurately than previously available. Implementations of the present disclosure also provide adaptation to disparate data sources storing data in different formats. Further, implementations provide a common data model to capture the inherent relationships among the data elements, the data model being optimized for information extraction and data analysis. Implementations also provide optimized routines/scripts for loading and analyzing data, and validated analysis procedures/processes to derive desired information in an efficient and timely manner.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DETAILED DESCRIPTION

Implementations of the present disclosure are generally directed to a computer-implemented platform that enables users to identify challenges with costs in the managed healthcare context. More particularly, the computer-implemented platform of the present disclosure combines high-power computing, which provides relatively faster processing, analytical modeling, and data visualization to address challenges in the managed healthcare context. As described in further detail herein, implementations of the present disclosure can include actions of receiving data from a plurality of data sources, the data relating to cost of providing healthcare, providing a data model based on the data, automatically processing the data model using non-parametric analysis to provide a non-parametric analysis result, the non-parametric analysis result including a first variable, and a second variable, automatically processing the data model to correlate at least the first variable of the non-parametric analysis result to the second variable of the non-parametric analysis result to provide a correlation result, automatically processing the correlation result using parametric analysis to provide a parametric analysis result, the parametric result including at least one variable that affects the cost of healthcare more than one or more other variables of a plurality of variables of the data model, and providing at least one data visualization for display, the at least one data visualization providing at least one graphical representation of the parametric analysis result.

In general, and as described in detail herein, implementations of the present disclosure leverage data models and analytical processes to provide data insights, and identify root causes of increased cost in the healthcare context. More particularly, implementations of the present disclosure enable data from disparate data sources, and/or in disparate data formats to be ingested and merged, and used to populate a data model that is processed in accordance with the data analysis techniques of the present disclosure to identify one or more variables affecting changes to cost of healthcare.

Figure 1:
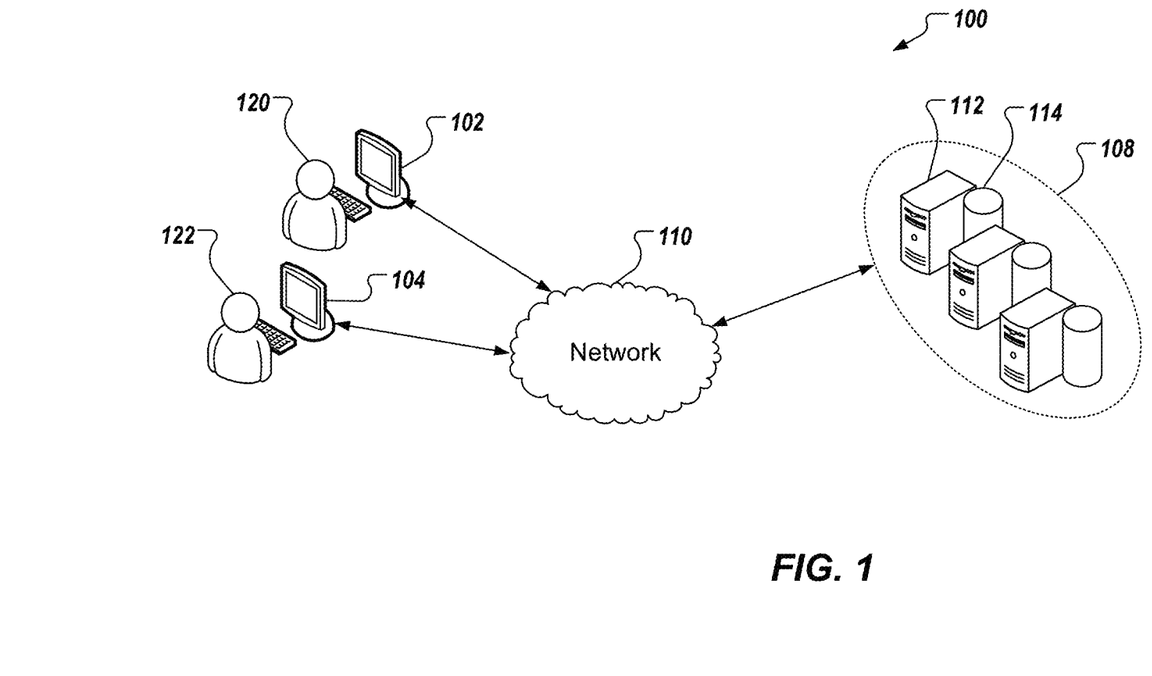
FIG. 1 depicts an example high-level architecture in accordance with implementations of the present disclosure.

FIG. 1 depicts an example system 100 that can execute implementations of the present disclosure. The example system 100 includes computing devices 102, 104, a back-end system 108, and a network 110. In some examples, the network 110 includes a local area network (LAN), wide area network (WAN), the Internet, or a combination thereof, and connects web sites, devices (e.g., the computing device 102, 104), and back-end systems (e.g., the back-end system 108). In some examples, the network 110 can be accessed over a wired and/or a wireless communications link. For example, mobile computing devices, such as smartphones can utilize a cellular network to access the network 110.

In the depicted example, the back-end system 108 includes at least one server system 112, and data store 114 (e.g., database and knowledge graph structure). In some examples, the at least one server system 112 hosts one or more computer-implemented services that users can interact with using computing devices. For example, the server system 112 can host a computer-implemented data analytics service for providing analytical processes to for data insights, and identifying root causes of increased cost in the healthcare context in accordance with implementations of the present disclosure.

In some examples, the computing devices 102, 104 can each include any appropriate type of computing device such as a desktop computer, a laptop computer, a handheld computer, a tablet computer, a personal digital assistant (PDA), a cellular telephone, a network appliance, a camera, a smart phone, an enhanced general packet radio service (EGPRS) mobile phone, a media player, a navigation device, an email device, a game console, or an appropriate combination of any two or more of these devices or other data processing devices.

In the depicted example, the computing devices 102, 104 are used by users 120, 122, respectively. In accordance with the example context, the users 120, 122 can include analysts that use the computing devices 102, 104 to interact with the computer-implemented data analytics service hosted in the back-end system 108. In some examples, and as described in further detail herein, data from disparate data sources, and/or in disparate data formats are processed through the data analytics service to provide one or more data visualizations to the users 120, 122, displayed on the computing devices 102, 104.

Figure 2:
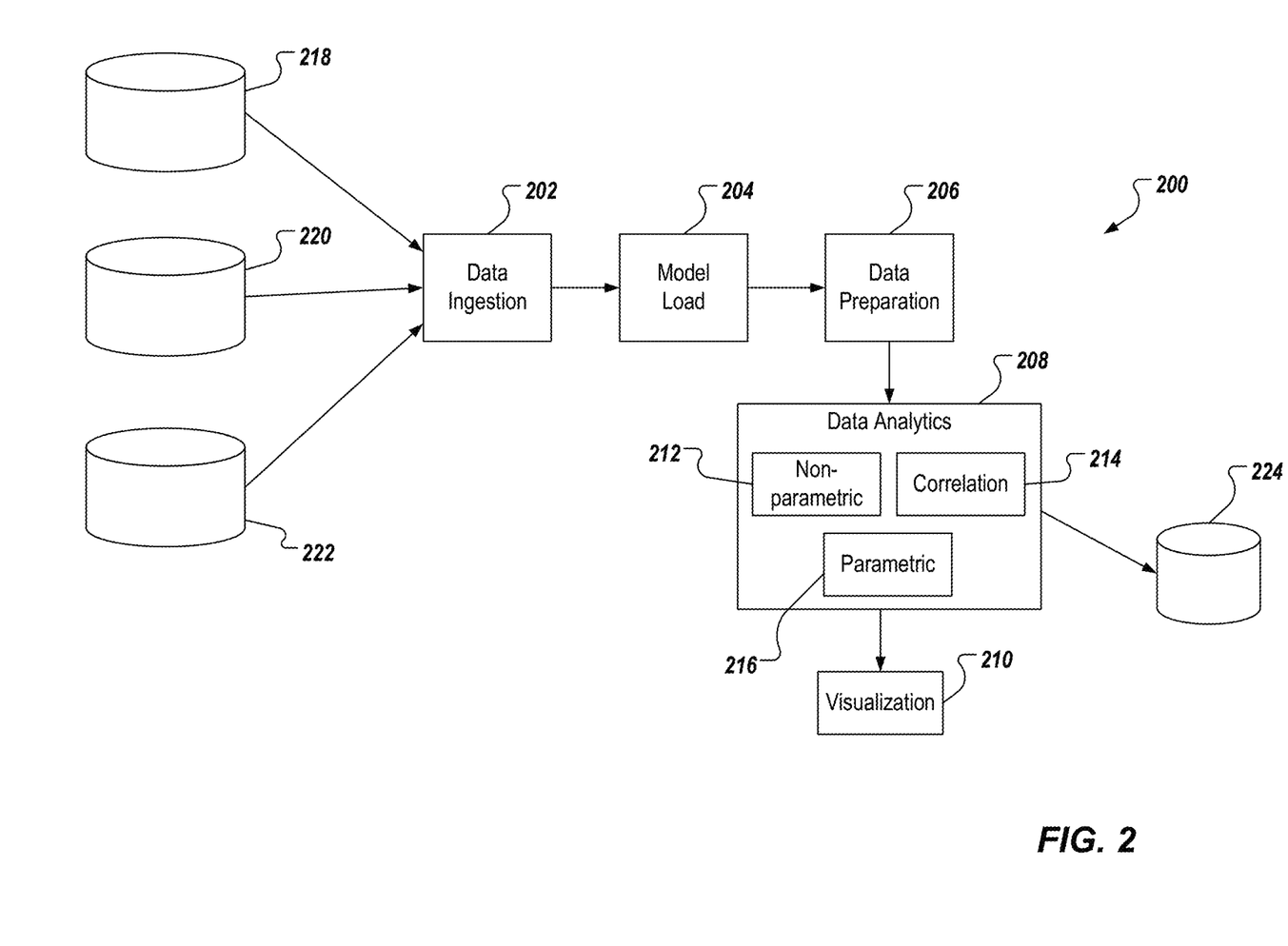
FIG. 2 depicts an example data analytics platform in accordance with implementations of the present disclosure.

FIG. 2 depicts an example data analytics platform 200 in accordance with implementations of the present disclosure. In some examples, the data analytics platform 200 can be hosted by one or more server systems 112 of FIG. 1. In the depicted example, the example data analytics platform 200 includes a data ingestion module 202, a model load module 204, a data preparation module 206, a data analytics module 208, and a visualization module 210. In the depicted example, the data analytics module 208 includes a non-parametric analysis module 212, a correlation module 214, and a parametric analysis module 216. In some examples, each module can be provided as one or more computer-executable programs executed using one or more computing devices. In some examples, the modules can be included in a single computer-executable program executed using one or more computing devices.

In accordance with implementations of the present disclosure, the data analytics platform 200 receives data from a plurality of data sources 218, 220, 222. In some examples, the data sources 218, 220, 222 provide data in disparate formats with respect to one another. In the example healthcare context, data provided from the data sources 218, 220, 222 can include data that is associated with healthcare costs. For example, the data sources 218, 220, 222 can include, without limitation, a claims database (e.g., storing data associated with claims submitted to an insurance company), a provider database (e.g., storing data associated with healthcare providers, such as doctors, hospitals, clinics), an auditing database (e.g., storing data associated with audits of claims), and a member database (e.g., storing data associated with in-network members and out-of-network members).

In some implementations, the data ingestion module 202 receives the data from the data source 218, 220, 222. In some examples, the data ingestion module 202 compares data sets from respective data sources, and connects data associated with the same entity. For example, an entity can include a healthcare provider, and data associated with the healthcare provider can be received from a claims database (e.g., claims submitted to an insurance company by the health provider), a provider database (e.g., unique identifier assigned to the healthcare provider by the insurance company, a unique identifier assigned to the healthcare provider by a third-party (National Provider Identifier (NPI), tax identification number (TIN)), billing address, etc.), an auditing database (e.g., date, reason, amount, etc., of adjustment for adjusted claims), and a member database (e.g., contract information for in-network provider). In some examples, the data is provided in respective data sets from the data sources 218, 220, 222, and one or more pointers are provided to indicate relationships between data across the data sets. For example, a provider data set can include data associated with respective healthcare providers (e.g., unique identifiers, billing addresses, etc.), and, for a particular provider, one or more pointers can point to data in another data set (e.g., claims data set) that correspond to the particular provider.

In some examples, a pointer is provided based on analyzing data across data sets to determine that data across multiple data sets correspond to the same provider. For example, a provider data set can indicate, by way of example, that Dr. Jones is a healthcare provider, and is assigned the NPI 0123456789, and the TIN 99-1234567, and has a billing address of 1234 Main St., Anytown, USA 12345. A claim data set can include data associated with a plurality of claims (e.g., hundreds, thousands of claims), and, for each claim, the claim data set can include the NIP, TIN, and billing address of the provider that submitted the claim, a unique claim identifier (claim ID), and data associated with the claim (e.g., date, amount, code(s) (Current Procedural Terminology (CPT) codes). An audit data set can include data associated with audits to claims (e.g., claim ID, date, adjustment).

In some examples, for each provider in the provider data set, other data sets are reviewed to provide pointers to associated data. For example, the claim data set can be reviewed based on the NPI, the TIN, and/or the billing address (e.g., zip code) of a provider to identify claims that are associated with the particular provider (e.g., claims submitted by the provider). In some examples, if two or more of the NPI, the TIN, and the billing address (e.g., zip code) of a provider correspond to a respective two or more of the NPI, the TIN, and the billing address (e.g., zip code) of a claim, a pointer is provided to indicate that the claim is associated with the provider. In some examples, the audit data set can be reviewed based on claim ID, date, amount, and/or code(s) to identify adjusted claims that correspond to original (source) claims. For example, if the claim ID, and one or more of date, amount, and/or code(s) corresponds to a claim ID and respective one or more of date, amount, and/or code(s) of an adjustment, a pointer is provided to indicate that the claim is associated with the adjustment. In this manner, multiple pointers can be provided linking a provider to claims, adjustments, and the like.

In some implementations, the model load module 204 populates an initial data model based on the data received from the data sources 218, 220, 222, and the pointers. In some examples, the initial data model is provided as a data structure (e.g., set of tables, each table having respective fields corresponding to attributes). In some examples, the data model models a generic claim process and relationships among the elements in the claim process. In some examples, the data model is not provider or payer specific, and captures information necessary for processing such data and make the processing more flexible, easy to use and provide a basis for subsequent analysis.

For example, the initial data model can include attributes such as claim ID, main claim, alternate claim, amount, date, claim adjustments, etc. In general, the initial data model includes attributes for the respective data received from the data sources 218, 220, 222. In some examples, one or more scripts are executed to load data into the initial data model based on the pointers. For example, for a particular provider, data from the provider data set can be loaded into the initial data model (e.g., fields of a respective table of the data model being populated with the respective data values), and data from the claims data set and/or audit data set pointed to by pointers can be loaded for the respective provider.

In some implementations, the data preparation module 206 processes the populated initial data model to prepare the data for analysis in the analytics module 208. For example, the data preparation module 206 processes the initial data model to provide a data model (modified data model). In some examples, data preparation includes checking quality of data, and ensuring data fields are populated. In some examples, a record can include multiple data fields (e.g., a claim record including claim ID field, date field, code(s) field, amount field). In some examples, if one or more fields of a record is absent a data value, the record is removed from the initial data model. For example, if a record of a claim is absent the claim ID, the record is removed from the initial data model. In this manner, only complete records are included in the data model. In some examples, data values are reviewed to ensure that the data value corresponds to an expected value. For example, a particular field of a record may require a string value having a particular format (e.g., claim ID), but it is determined that the field includes an integer value, and/or does not conform to the particular format. Consequently, the record is removed from the initial data model. In this manner, the accuracy of records remaining in the data model is improved.

In some implementations, the cost of healthcare can be determined based on the following example relationship:

$$\Delta d = A*B*C*D*E$$

where:

A indicates change in membership (e.g., customers) and is provided as $\Delta m$;

B and C represent utilization, B indicating % change in members with claims and is provided as $$\Delta\left(\frac{u}{m}\right),$$

and C indicating change in member utilization and is provided as $$\Delta\left(\frac{c}{u}\right);$$

D and E represent cost, D indicating change in claim paid/denial rate and is provided as $$\Delta\left(\frac{p}{c}\right),$$

and E indicating change in amount paid per claim and is provided as $$\Delta\left(\frac{d}{p}\right);$$

m is the total number of members;
u is members with claims;
p is a count of paid claims;
d is total paid (e.g., in US dollars); and
c is the count of all claims.

In accordance with implementations of the present disclosure, the data analytics module 208 processes the data model to identify variables (e.g., of the above, example relationship) influencing changes in cost of healthcare. In general, and as described in further detail herein, the data model is processed to identify variables causing changes (e.g., increase) in healthcare costs.

In some implementations, the non-parametric analysis module 212 processes the data model to provide a non-parametric analysis result. In some examples, the non-parametric analysis result is a data set indicating one or more variables (factors) that likely affect the cost of healthcare. In general, the non-parametric analysis result provides a subset of variables (factors) that can be focused on in subsequent stages of data analytics from a set of variables. For example, the data model can provide data values for twenty variables associated with cost of healthcare. Processing all twenty variables across all values for each variable can be time and resource intensive (e.g., significant technical resources (processors, memory, bandwidth) may be required to perform data analytics on all variables). In accordance with implementations of the present disclosure, the non-parametric analysis provides a sub-set of variables (e.g., ten of the twenty variables), which can be used as the starting point for subsequent data analysis stages. In this manner, the resources required to perform the subsequent data analytics can be reduced (e.g., less processors, memory, bandwidth than without the non-parametric analysis).

In some implementations, non-parametric analysis is based on unknown distributions of the data records, and values of the variables across the records. Non-parametric analysis generally refers to a class of statistical analyses that do not rely on assumptions about the shape or form of the probability distribution from which the data were drawn. In some implementations, the non-parametric analysis uses Markov Chain Monte Carlo (MCMC) simulation, which enables analysis to be performed without making specific assumptions about the underlying distribution, and is adaptive to many different situations in which analysis is needed.

In some examples, during non-parametric analysis, individual variables are reviewed based on a variable's values across the data records, and a respective score is determined. An example score can include a p-value. In some examples, a p-value is the probability of obtaining a value equal to or greater than the value observed. In some examples, a p-value is used to determine whether results are within a normal range of values for events being observed. For example, if a p-value of a variable is above a predetermined threshold it can be determined that the variable, to which the p-value corresponds, has a meaningful effect on the results (e.g., change in healthcare cost). In accordance with implementations of the present disclosure, a set of scores is determined using non-parametric analysis, each score in the set of scores corresponding to a respective variable. Each score (e.g., p-value) is compared to a threshold score, and if the score exceeds the threshold score, the respective variable is included in the sub-set of variables.

In accordance with implementations of the present disclosure, the non-parametric analysis results (e.g., sub-set of variables) is provided to the correlation module 214, which processes the non-parametric analysis results to provide a correlation result. In some examples, the correlation result is provided as a sub-set of variables that correlate to one another. For example, the correlation analysis begins with the sub-set of variables provided from the non-parametric analysis (e.g., ten of the twenty variables), and determines a measure of correlation (correlation value) between a variable and on or more other variables. Example correlation values include, without limitation, the correlation coefficient (Pearson's), and rank correlation coefficient (Spearman's, Kendall's). In some examples, the correlation value can be provided as a p-value for particular combinations of variables.

In some implementations, the one or more other variables include variables provided in the sub-set of variables (e.g., ten of the twenty variables), and variables in the original set of variables (e.g., all twenty variables ($V_1, \ldots, V_{20}$)). For example, the sub-set of variables can include $V_1$, $V_5$, $V_8$, $V_{10}$, $V_{12}$, $V_{14}$, $V_{15}$, $V_{17}$, $V_{19}$, $V_{20}$. The correlation analysis can be performed to provide correlation values between $V_1$ and each of $V_2, \ldots V_{20}$, $V_5$ and each of $V_1, \ldots V_4$ and $V_6, \ldots V_{20}$, $V_8$ and each of $V_1, \ldots V_7$ and $V_9, \ldots V_{20}$, and so on. In some examples, the correlation analysis can be performed to provide correlation values between combinations of variables of the sub-set of variables, and one or more other variables in the set of variables. For example, respective correlation values can be determined between $V_1$ and $V_5$, and one or more of $V_2, \ldots V_4$ and $V_6, \ldots V_{20}$, $V_1$ and $V_8$, and one or more of $V_2, \ldots V_7$ and $V_9, \ldots V_{20}$, $V_1$, $V_5$, and $V_8$, and one or more of $V_2, \ldots V_4$, $V_6$, $V_7$, and $V_9, \ldots V_{20}$, and so on.

In some implementations, each correlation value is compared to a threshold correlation value. If the correlation value exceeds a threshold correlation value, the respective combination of variables is included in the correlation result. For example, it can be determined that the combinations of ($V_1$, $V_8$, $V_{13}$), ($V_1$, $V_8$, $V_{16}$), ($V_1$, $V_5$, $V_{11}$), among others, each include correlation values exceeding the threshold correlation value. Consequently, at least these combinations of variables are included in the correlation result.

In accordance with implementations of the present disclosure, the correlation result is provided as input to the parametric analysis module 216. In some implementations, the parametric analysis module 216 processes the correlation result to provide a parametric analysis result. In some examples, parametric analysis includes a sub-set of variables that significantly affect the cost of healthcare. Parametric analysis generally refers to a class of statistical analyses that rely on assumptions about the shape of the distribution (e.g., normal distribution assumed) in the underlying population, as well as assumptions about the form or parameters (e.g., means and standard deviations) of the assumed distribution.

In some implementations, the parametric analysis result is fed back into the correlation analysis, or the parametric analysis. In some examples, the parametric analysis is iteratively performed to hone in on one or more variables that have the most significant impact in change to cost of healthcare. In some implementations, iterations are repeated a number of times until a threshold number of samples is achieved. In some examples, the threshold number of samples is based on a desired confidence level.

In some implementations, the results of each of the data analysis stages (e.g., non-parametric analysis, correlation, parametric analysis) are stored in a database 224. In some examples, the results of one or more of the data analysis stages are provided to the data visualization module 210, which provides one or more data visualizations based on the results. For example, the visualization module 210 can provide instructions to a device (e.g., a client-side computing device), the instructions being executable by the device to display at least one data visualization providing at least one graphical representation based on one or more of the results.

Figure 3A:
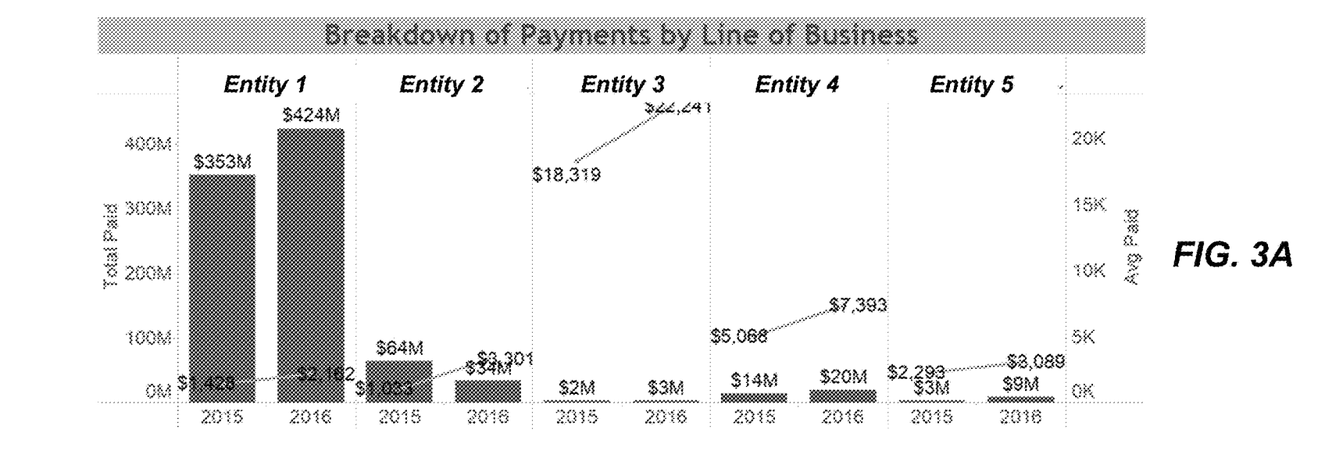
FIGS. 3A-3F depict example visualizations in accordance with implementations of the present disclosure.
Figure 3B:
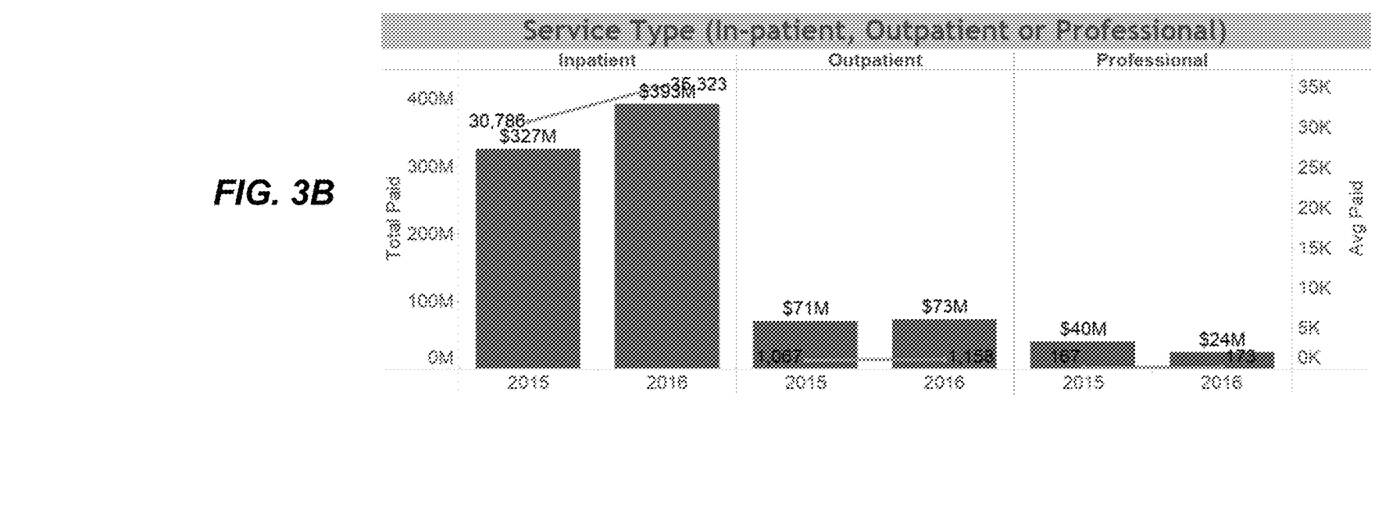
Figure 3C:
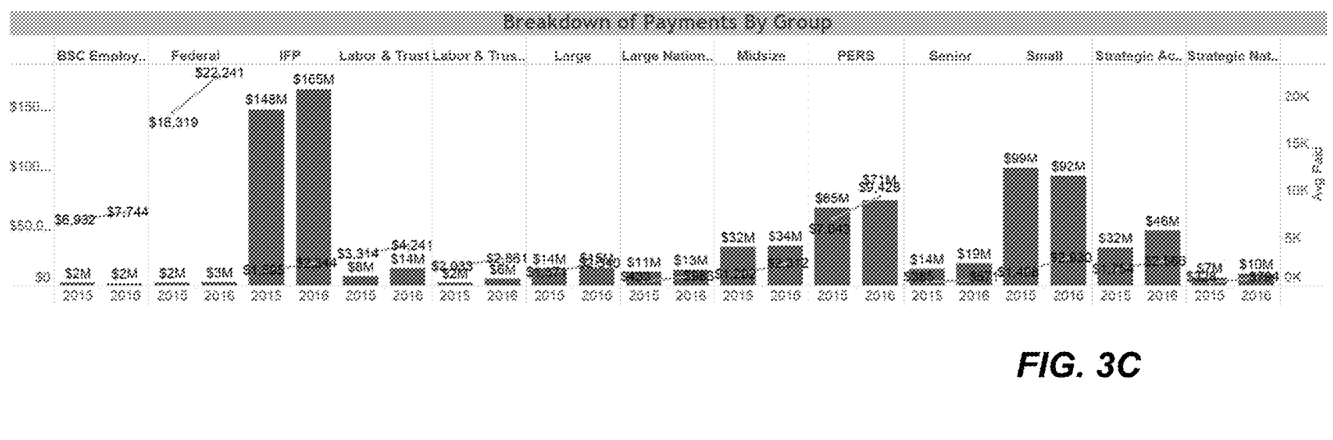
Figure 3D:
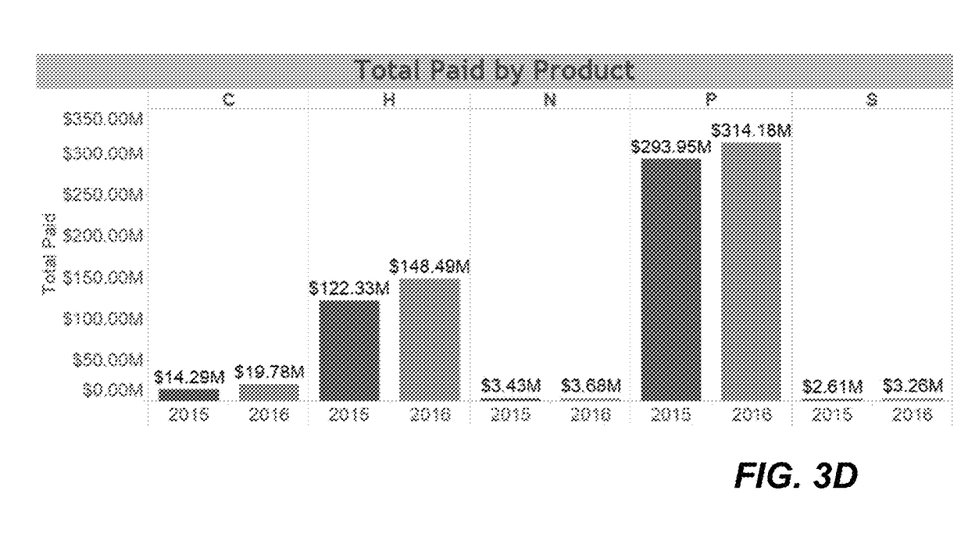
Figure 3E:
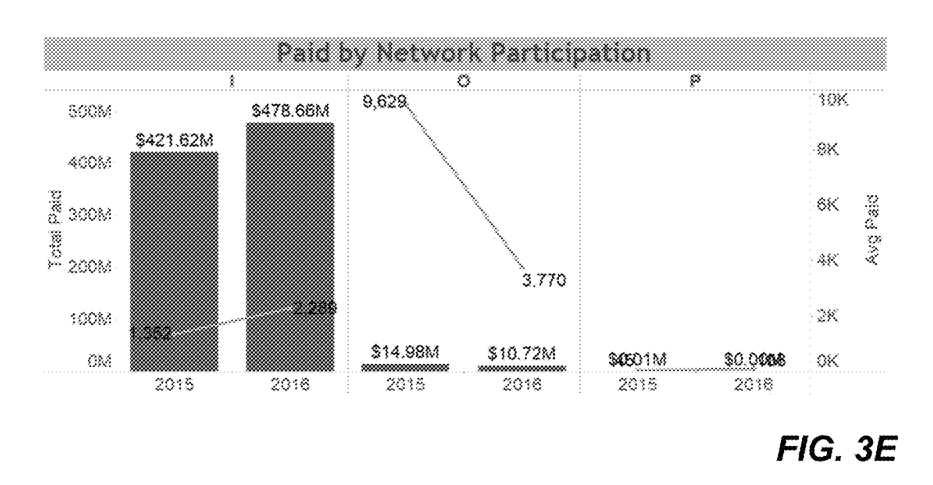
Figure 3F:
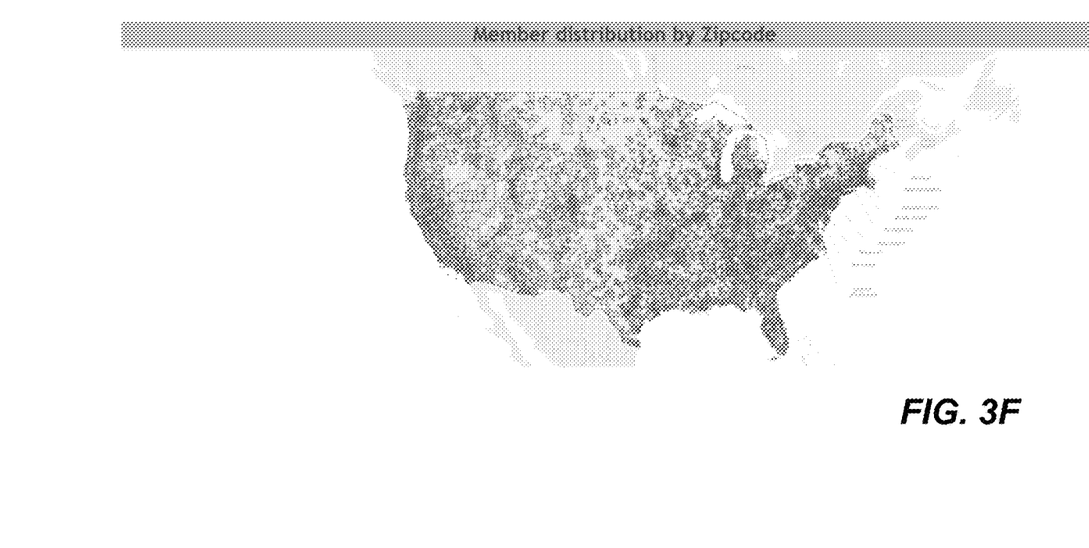

FIGS. 3A-3F depict example visualizations in accordance with implementations of the present disclosure. In general, FIGS. 3A-3F provide respective views on dimensional analysis. For example, FIGS. 3A-3E provide bar graphs depicting effects on cost across respective metrics (e.g., line of business, service type, group, product, network participation). FIG. 3F provides a graphical representation of geographical distribution on members.

Figure 4:
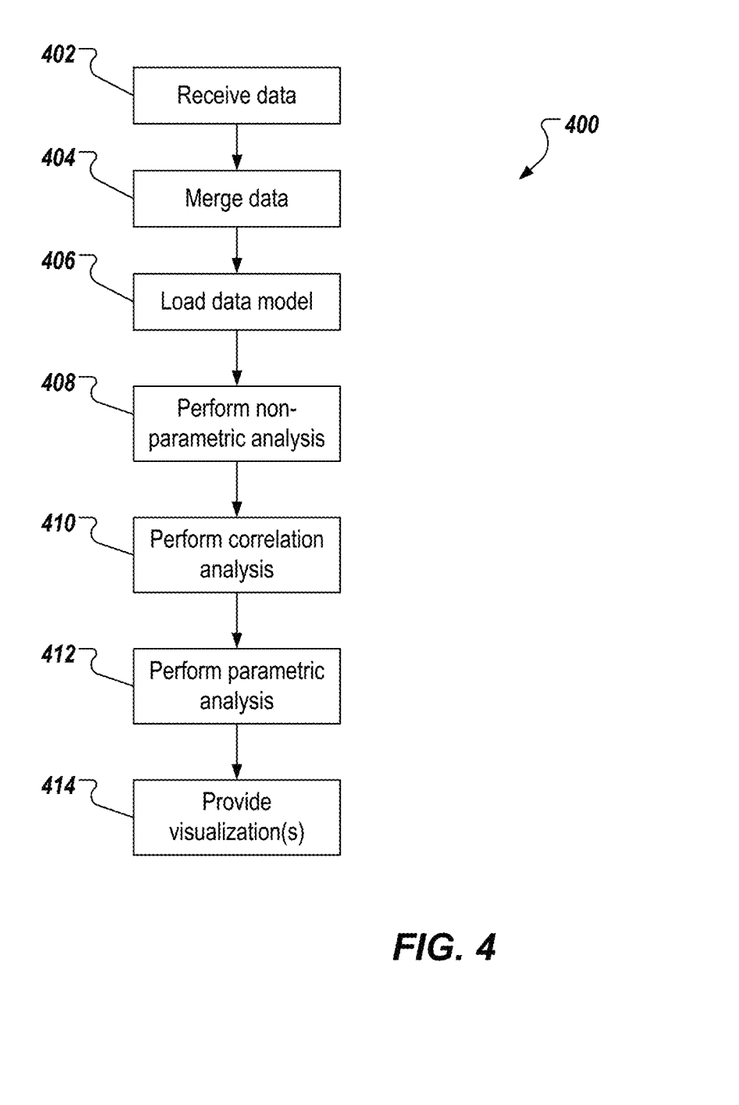
FIG. 4 depicts an example process that can be executed in implementations of the present disclosure.

FIG. 4 depicts an example process 400 that can be executed in implementations of the present disclosure. In some examples, the example process 400 is provided using one or more computer-executable programs executed by one or more computing devices (e.g., the back-end system 108 of FIG. 1). The example process 400 can be executed to provide data analytics in accordance with implementations of the present disclosure.

Data is received (402). For example, the data ingestion module 202 of FIG. 2 receives data from the data sources 218, 220, 222. Data is merged (404). For example, the data ingestion module 202 analyzes the data sets provided from the data source 218, 220, 222, and associates data with one another across data sets (e.g., provides pointers, as described herein). A data model is loaded (406). For example, the model load module 204 retrieves an unpopulated data model from computer-readable memory, and executes one or more scripts to populate the data model with the data received from the data sources 218, 220, 222. In some examples, the data preparation module 206 prepares the data model for data analysis (e.g., reviews the populated data model, and selectively deletes records from the data model, as described herein).

Non-parametric analysis is performed (408). For example, the non-parametric analysis module 212 receives the data model, and processes the data model using non-parametric analysis techniques to provide a non-parametric analysis result. In some examples, the non-parametric analysis result includes a sub-set of variables of a set of variables of the data model. Correlation analysis is performed (410). For example, the correlation module 214 receives the non-parametric analysis result, and processes the non-parametric result using correlation techniques to provide a correlation result. In some examples, the correlation result includes one or more sets of variable that correlate with one another. Parametric analysis is performed (412). For example, the parametric analysis module 216 receives the correlation result, and processes the correlation result using parametric analysis techniques to provide a parametric analysis result. In some examples, the parametric analysis result can be fed back to the correlation analysis, or the parametric analysis to further hone in on one or more variables that significantly affect changes in healthcare costs, relative to other variables in the data model.

Data visualizations are provided (414). For example, and as described herein, the results of each of the data analysis stages (e.g., non-parametric analysis, correlation, parametric analysis) are stored in a database (e.g., the database 224). In some examples, the results of one or more of the data analysis stages are provided to the data visualization module 210, which provides one or more data visualizations based on the results. For example, the visualization module 210 can provide instructions to a device (e.g., a client-side computing device), the instructions being executable by the device to display at least one data visualization providing at least one graphical representation based on one or more of the results.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a stand alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a Web browser through which a user may interact with an implementation, or any appropriate combination of one or more such back end, middleware, or front end components. The components of the system may be interconnected by any appropriate form or medium of digital data communication (e.g., a communication network). Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A computer-implemented method for identifying one or more variables affecting a cost of healthcare, the method being executed by one or more processors and comprising:

receiving, by the one or more processors, data from a plurality of data sources, the data relating to cost of providing healthcare;

providing, by the one or more processors, a data model based on the data;

automatically, by the one or more processors, processing the data model using non-parametric analysis to provide a non-parametric analysis result, the non-parametric analysis result comprising a sub-set of variables of a plurality of variables of the data model, each variable in the non-parametric analysis result having a respective score that exceeds a threshold score, the sub-set of variables comprising:
a first variable, and
a second variable;

automatically, by the one or more processors, processing the data model to correlate at least the first variable of the non-parametric analysis result to the second variable of the non-parametric analysis result to provide a correlation result;

automatically, by the one or more processors, processing the correlation result using parametric analysis to provide a parametric analysis result, the parametric analysis result comprising:
at least one variable that affects the cost of healthcare more than one or more other variables of the plurality of variables of the data model; and providing, by the one or more processors, at least one data visualization for display, the at least one data visualization providing at least one graphical representation of the parametric analysis result.

2. The method of claim 1, further comprising:
providing an initial data model based on the data received from the plurality of data sources; and
selectively deleting one or more data records from the initial data model to provide the data model.

3. The method of claim 1, wherein the respective score comprises a p-value.

4. The method of claim 1, wherein the correlation result comprises a plurality of sets of variables, each set of variables in the correlation result having a respective score indicating a correlation between variables in the set of variables that exceeds a threshold score.

5. The method of claim 1, wherein the data model comprises a plurality of tables that are populated with a plurality of data values for each variable of the plurality of variables.

6. The method of claim 1, further comprising:
storing each of the non-parametric analysis result, the correlation result, and the parametric analysis result in a database; and
providing one or more data visualizations for each of the non-parametric analysis result, and the correlation result.

7. One or more non-transitory computer-readable storage media coupled to one or more processors and having instructions stored thereon which, when executed by the one or more processors, cause the one or more processors to perform operations for identifying one or more variables affecting a cost of healthcare, the operations comprising:

receiving, by the one or more processors, data from a plurality of data sources, the data relating to cost of providing healthcare;

providing, by the one or more processors, a data model based on the data;

automatically, by the one or more processors, processing the data model using non-parametric analysis to provide a non-parametric analysis result, the non-parametric analysis result comprising a sub-set of variables of a plurality of variables of the data model, each variable in the non-parametric analysis result having a respective score that exceeds a threshold score, the sub-set of variables comprising:
a first variable, and
a second variable;
automatically, by the one or more processors, processing the data model to correlate at least the first variable of the non-parametric analysis result to the second variable of the non-parametric analysis result to provide a correlation result;
automatically, by the one or more processors, processing the correlation result using parametric analysis to provide a parametric analysis result, the parametric analysis result comprising:
at least one variable that affects the cost of healthcare more than one or more other variables of a plurality of variables of the data model; and
providing, by the one or more processors, at least one data visualization for display, the at least one data visualization providing at least one graphical representation of the parametric analysis result.

8. The non-transitory computer-readable storage media of claim 7, wherein operations further comprise:
providing an initial data model based on the data received from the plurality of data sources; and
selectively deleting one or more data records from the initial data model to provide the data model.

9. The non-transitory computer-readable storage media of claim 7, wherein the respective score comprises a p-value.

10. The non-transitory computer-readable storage media of claim 7, wherein the correlation result comprises a plurality of sets of variables, each set of variables in the correlation result having a respective score indicating a correlation between variables in the set of variables that exceeds a threshold score.

11. The non-transitory computer-readable storage media of claim 7, wherein the data model comprises a plurality of tables that are populated with a plurality of data values for each variable of the plurality of variables.

12. The non-transitory computer-readable storage media of claim 7, wherein operations further comprise:
storing each of the non-parametric analysis result, the correlation result, and the parametric analysis result in a database; and
providing one or more data visualizations for each of the non-parametric analysis result, and the correlation result.

13. A system, comprising:
one or more processors; and
a computer-readable storage device coupled to the one or more processors and having instructions stored thereon which, when executed by the one or more processors, cause the one or more processors to perform operations for identifying one or more variables affecting a cost of healthcare, the operations comprising:
receiving, by the one or more processors, data from a plurality of data sources, the data relating to cost of providing healthcare;
providing, by the one or more processors, a data model based on the data;
automatically, by the one or more processors, processing the data model using non-parametric analysis to provide a non-parametric analysis result, the non-parametric analysis result comprising a sub-set of variables of a plurality of variables of the data model, each variable in the non-parametric analysis result having a respective score that exceeds a threshold score, the sub-set of variables comprising:
a first variable, and
a second variable;
automatically, by the one or more processors, processing the data model to correlate at least the first variable of the non-parametric analysis result to the second variable of the non-parametric analysis result to provide a correlation result;
automatically, by the one or more processors, processing the correlation result using parametric analysis to provide a parametric analysis result, the parametric analysis result comprising:
at least one variable that affects the cost of healthcare more than one or more other variables of a plurality of variables of the data model; and
providing, by the one or more processors, at least one data visualization for display, the at least one data visualization providing at least one graphical representation of the parametric analysis result.

14. The system of claim 13, wherein operations further comprise:
providing an initial data model based on the data received from the plurality of data sources; and
selectively deleting one or more data records from the initial data model to provide the data model.

15. The system of claim 13, wherein the respective score comprises a p-value.

16. The system of claim 13, wherein the correlation result comprises a plurality of sets of variables, each set of variables in the correlation result having a respective score indicating a correlation between variables in the set of variables that exceeds a threshold score.

17. The system of claim 13, wherein the data model comprises a plurality of tables that are populated with a plurality of data values for each variable of the plurality of variables.

* * * * *

UNITED STATES PATENT AND TRADEMARK OFFICE
CERTIFICATE OF CORRECTION

PATENT NO. : 10,699,808 B2
APPLICATION NO. : 15/369329
DATED : June 30, 2020
INVENTOR(S) : Perry et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 510 days.

Signed and Sealed this
Thirty-first Day of January, 2023

*Katherine Kelly Vidal*

Katherine Kelly Vidal
*Director of the United States Patent and Trademark Office*